(12) United States Patent
Musaeus et al.

(10) Patent No.: US 10,440,983 B2
(45) Date of Patent: Oct. 15, 2019

(54) MICROCAPSULES COMPRISING LUTEIN OR LUTEIN ESTER

(71) Applicant: BASF SE, Ludwigshafen (DE)

(72) Inventors: Nina Musaeus, Hellerup (DK); Inge-Lise Krylbo, Søborg (DK)

(73) Assignee: BASF SE (DE)

( * ) Notice: Subject to any disclaimer, the term of this patent is extended or adjusted under 35 U.S.C. 154(b) by 0 days.

(21) Appl. No.: 15/549,028

(22) PCT Filed: Feb. 8, 2016

(86) PCT No.: PCT/EP2016/052620
§ 371 (c)(1),
(2) Date: Aug. 4, 2017

(87) PCT Pub. No.: WO2016/124785
PCT Pub. Date: Aug. 11, 2016

(65) Prior Publication Data
US 2018/0027865 A1    Feb. 1, 2018

(30) Foreign Application Priority Data

Feb. 6, 2015    (EP) .................................... 15154156

(51) Int. Cl.
| | | |
|---|---|---|
| *A23P 10/30* | (2016.01) | |
| *A61K 31/07* | (2006.01) | |
| *A23L 29/281* | (2016.01) | |
| *A23L 5/44* | (2016.01) | |
| *A23L 33/155* | (2016.01) | |
| *A61K 9/14* | (2006.01) | |
| *A61K 9/16* | (2006.01) | |
| *A61K 31/23* | (2006.01) | |
| *A23L 33/12* | (2016.01) | |
| *A61K 9/50* | (2006.01) | |
| *A61K 31/015* | (2006.01) | |
| *A61K 31/047* | (2006.01) | |

(52) U.S. Cl.
CPC .................. *A23P 10/30* (2016.08); *A23L 5/44* (2016.08); *A23L 29/284* (2016.08); *A23L 33/12* (2016.08); *A23L 33/155* (2016.08); *A61K 9/146* (2013.01); *A61K 9/1676* (2013.01); *A61K 9/5057* (2013.01); *A61K 9/5063* (2013.01); *A61K 31/015* (2013.01); *A61K 31/047* (2013.01); *A61K 31/07* (2013.01); *A61K 31/23* (2013.01); *A23V 2002/00* (2013.01); *A23V 2250/5432* (2013.01)

(58) Field of Classification Search
None
See application file for complete search history.

(56) References Cited

U.S. PATENT DOCUMENTS

| | | | |
|---|---|---|---|
| 5,478,569 A | 12/1995 | Berneis et al. | |
| 5,780,056 A | 7/1998 | Akamatsu et al. | |
| 6,077,540 A * | 6/2000 | Daher .................... | A61K 9/282 |
| | | | 424/464 |
| 9,357,796 B2 | 6/2016 | Musaeus et al. | |
| 2003/0148099 A1* | 8/2003 | DeFreitas ................ | B01J 13/04 |
| | | | 428/402.2 |
| 2006/0051479 A1 | 3/2006 | Chiavazza et al. | |
| 2006/0165990 A1 | 7/2006 | Curtis et al. | |
| 2008/0026124 A1 | 1/2008 | Musaeus et al. | |
| 2010/0303913 A1 | 12/2010 | Gheith et al. | |

FOREIGN PATENT DOCUMENTS

| | | | |
|---|---|---|---|
| CA | 2919468 A1 | 1/2015 | |
| CN | 102389108 A | 3/2012 | |
| CN | 103735532 A | 4/2014 | |
| EP | 347751 A1 | 12/1989 | |
| EP | 1105099 A2 | 6/2001 | |
| EP | 1794238 B1 | 7/2008 | |
| EP | 1938807 A1 | 7/2008 | |
| EP | 1898721 B1 | 2/2010 | |
| WO | WO-9106292 A1 | 5/1991 | |
| WO | WO-0010525 A2 * | 3/2000 | ........... A61K 9/2063 |
| WO | WO-0010525 A3 | 3/2000 | |
| WO | WO-2014154788 A1 | 10/2014 | |

OTHER PUBLICATIONS

International Search Report for PCT/EP2016/052619 dated Apr. 7, 2016.
International Search Report for PCT/EP2016/052620 dated Apr. 28, 2016.
Written Opinion of the International Searching Authority for PCT/EP2016/052619 dated Apr. 7, 2016.
Written Opinion of the International Searching Authority for PCT/EP2015/052620 dated Apr. 28, 2016.

* cited by examiner

*Primary Examiner* — Jake M Vu
(74) *Attorney, Agent, or Firm* — Drinker Biddle & Reath LLP

(57) ABSTRACT

The invention relates to a microcapsule comprising at least one active substance selected from lutein and lutein esters embedded in a matrix comprising fish gelatine and optionally one or more other matrix components, wherein the content of said at least one active substance calculated as free lutein is from 0.5 to 25% of total weight of the microcapsule, and which microcapsule does not comprise any added emulsifier.

The invention further relates to a process of preparing the microcapsule as well as uses and products comprising the microcapsule.

20 Claims, 2 Drawing Sheets

MICROCAPSULES COMPRISING LUTEIN OR LUTEIN ESTER

CROSS-REFERENCE TO RELATED APPLICATIONS

This application is a national stage application (under 35U.S.C. § 371) of PCT/EP2016/052620, filed Feb. 8, 2016, which claims benefit of European Application No. 15154156.2, filed Feb, 6, 2015, both of which are incorporated herein by reference in their entirety.

FIELD OF THE INVENTION

The present invention relates to a microcapsule comprising lutein or lutein esters as active substance embedded in a hydrocolloid matrix of fish gelatine, preferably low bloom fish gelatine, a process for preparing such microcapsules as well as applications thereof and products comprising such microcapsules.

BACKGROUND OF THE INVENTION

Lutein is a xanthophyll and a naturally occurring carotenoid found in plants, such as flowers, in particular marigold flowers, and green leafy vegetables. Lutein may for instances be extracted from the petals of marigold, spinach, kale and broccoli. Marigold is in particular rich in lutein, and it is found as lutein esters with fatty adds. Lutein can be used as yellow pigment in all kind of compositions, such as functional foods and health care products, and it has well known pharmacological effects and applications.

Lutein as free lutein has the chemical structure

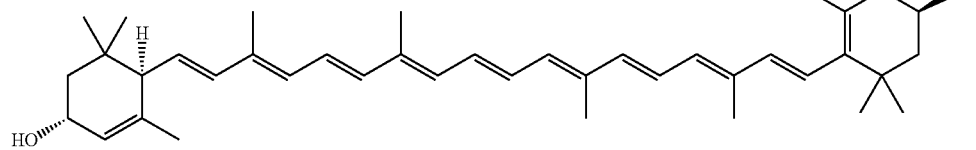

The typical lutein esters found in marigold are the mono- or dipalmitate, and these esters have properties different from the free lutein. The molecular weight of free lutein is about 569 g/mol, whereas the molecular weight of the dipalmitate is about 1046 g/mol.

The melting point of free lutein is about 190° C., whereas the melting range of the mixed naturally occurring lutein esters is from about 50 to about 80° C.

Chinese patent application 102389108 A discloses lutein ester microcapsule powder comprising lutein ester crystals, antioxidants and emulsifying agents for both the oil-phase and the aqueous-phase, filler, wall material and oil, and a method for preparing the same.

The filler material applied is modified gum arabic or modified starch. The application claims that both a water soluble and a oil soluble emulsifier are needed to produce the microcapsule powder. Using emulsifiers in the formulation has the disadvantages that air will be trapped into the powder particles and form hollow spheres. The included air and the porosity of the microcapsules lead to chemical degradation of the lutein or lutein ester. Using emulsifiers furthermore has the disadvantage that the preparation is more expensive and time consuming to produce because the emulsifiers have to be mixed thoroughly with the other ingredients in the aqueous and the oil phase, respectively. Furthermore the list of ingredients in the powder formulation increases.

EP 1 794 238 B1 discloses a carotenoid-containing dry powder comprising one or more carotenoids such as crystalline lutein obtainable by a microencapsulation process using isomalt and a protective colloid such as modified starch as encapsulation material, wherein the initial suspension of crystalline carotenoids is grounded.

EP 1 898 721 B1 discloses an aqueous carotenoid-containing suspension comprising at least one or more carotenolds such as crystalline lutein, modified starch and sucrose, wherein the initial suspension of crystalline carotenoids is grounded.

WO2014/154788 discloses a powderous composition comprising particles of lutein and maltodextrin as matrix material.

The main object of the present invention is to provide improved products based on lutein or lutein ester concentrates and fish gelatine which shall have a cleaner label and fewer ingredients. They shall have or create in the final product a more intense and longer lasting colour impression and they shall be more stable and less sensitive to oxidation compared with state of the art products. They shall exhibit a surface, said surface being more adapted for compression than surfaces of products of the prior art. They shall exhibit a greater chemical stability and be more natural in composition. They shall be produced in an easier and more cost effective way.

Another object is to provide improved products based on lutein or lutein ester concentrates and fish gelatine which can be used in tablets, dairies, such as milk products, and beverages with high stability due to proper encapsulation of the lutein and/or lutein ester and with improved oxygen barrier properties.

It is also an object to provide products with good colouring properties.

Yet another object is to provide a cost effective method for producing such products.

SUMMARY OF THE INVENTION

The present invention relates to a microcapsule comprising at least one active substance selected from lutein and lutein esters, embedded in a matrix comprising fish gelatine, preferably low bloom fish gelatine, and optionally one or more other matrix components, wherein the content of said at least one active substance calculated as free lutein is from 0.5 to 25% of total weight of the microcapsule, and which microcapsule does not comprise any added emulsifier.

In particular, the microcapsule does not comprise any added oil phase emulsifier.

It has surprisingly been found that the microcapsule of the invention can be provided without any added dispersing agent or emulsifier in addition to the fish gelatine.

Accordingly, the fish gelatine is the sole agent with dispersing properties present in the microcapsule. Traditionally, and according to prior art, also a classical emulsifier is included in a microcapsule to ensure a sufficiently small particle size, and a small particle size is important for the appearance and colour of the final product comprising the microcapsules, such as dairies and beverages. The absence of any added classical emulsifier has also the advantage in comparison with prior art microcapsules comprising lutein and lutein esters that foaming during preparation is avoided. Foaming during preparation will lead to inclusion of air in the microcapsules which will decrease the chemical stability of the lutein or lutein ester in the final product. Finally, a product without any added emulsifier provides the advantage of a cleaner label.

The present invention in another aspect relates to a process of preparing a microcapsule according to the invention, which process comprises the steps of
- melting or dissolving lutein or lutein ester concentrate(s),
- providing an aqueous solution of fish gelatine, preferably low bloom fish gelatine, and said optionally other matrix components,
- mixing said aqueous solution and said melted or dissolved lutein or lutein ester concentrate(s),
- homogenising the resulting preparation without addition of an emulsifier,
- finely dividing and drying the mixture thus obtained to prepare a mass of particles each containing lutein or lutein ester(s) embedded in said fish gelatine, preferably low bloom fish gelatine.

In a third aspect the invention relates to microcapsules according to the invention obtainable according to the process of the invention.

In a fourth aspect the invention relates to products comprising the microcapsule of the invention, in particular dairies, beverages and tablets.

Definitions

In the context of the current invention, the following terms are meant to comprise the following, unless defined elsewhere in the description.

Lutein ester concentrate is a dark orange-brown oleoresin or a granular powder having a melting range of approximately 50-80° C. It typically comprises 70-85% lutein ester, corresponding to about half the amount of free lutein. It can be dissolved or melted in oil.

Lutein ester concentrate complies with the EFSA (European Food Safety Authority) specification for lutein (Directive 2008/128/EC (E 161b)). The main colouring principle of lutein consists of carotenoids of which lutein and its fatty esters account for the major part.

Variable amounts of other carotenes and xanthophyll esters, such as zeaxanthin ester, are also present in the concentrate. Lutein may contain fats, oils and waxes naturally occurring in the plant material. Lutein ester concentrate contains min. 60% total carotenoid esters.

Fish gelatine is in this context defined as a protective hydrocolloid with dispersing properties. In the context of the present invention it is not to be understood as a classical emulsifier (surfactant) in accordance with the definition below.

Low bloom, medium bloom and high bloom fish gelatines are gelatins having a strength of less than about 120 bloom (low bloom), between 120 and 200 bloom (medium bloom) or a strength of more than about 200 bloom (high bloom.)

Low bloom fish gelatine in particular means a fish gelatine having a strength of 100 bloom or less, more preferably 80 bloom or less, more preferably from zero to 80 bloom, still more preferred from zero bloom to 50 bloom.

In a more preferred embodiment low bloom fish gelatine means a fish gelatine having a strength of about 50 bloom or less, preferably of about 30 bloom or less, more preferably of about 20 bloom or less and further preferred of about 10 bloom or less.

A particular preferred embodiment of low bloom fish gelatine comprises a fish gelatine having a strength of zero bloom.

An emulsifier is defined as a substance with a hydrophilic head and a hydrophobic tail. Emulsifiers can be divided into non-ionic, anionic and cationic emulsifiers. Depending on the HLB-value (hydrophilic-lipophilic balance) emulsifiers can be either oil soluble (low HLB values) or water soluble (high HLB values). Adding both types to an emulsion often works synergistic. Typical emulsifiers allowed in food products comprise glycerol fatty acid esters, sucrose fatty acid esters, sorbitan fatty acid esters, lecithins, ascorbyl palmitate and ascorbyl stearate.

Dispersing means mixing one phase (the continuous phase) with a second phase (the disperse phase) where the two phases not being miscible to prepare a dispersion. The nature of each phase can be liquid, solid or gaseous.

Homogenising means treating a dispersion in order to reduce the size of the droplets/particles of the disperse phase.

Bloom is a test to measure the strength of a gel of gelatine. The test determines the weight (in grams) needed by a probe (normally with a diameter of 0.5 inch) to deflect the surface of the gel 4 mm without breaking it. The result is expressed in bloom (grades).

Morphology means the shape and structure of a physical object, in the context of this invention the shape and structure of a microcapsule.

The color strength ($E^{0.1\%}_{1cm}$-value) is here defined as the absorption of a 1% aqueous dispersion of a 10% lutein or lutein ester dry powder measured in a 1 cm cuvette at the wavelength of the absorption maximum.

Tablet stability means the chemical stability of lutein or lutein ester added as a microencapsulated powder to multivitamin mineral tablets stored under controlled conditions and followed over time.

Figures

The appearance and surface morphology of the microcapsules of the invention in comparison with FloraGLO® Lutein 10% VG TabGrade microcapsules from Kemin Health, L.C. are illustrated in FIG. 1 and FIG. 2, wherein.

DETAILED DESCRIPTION OF THE INVENTION

Figure 1:
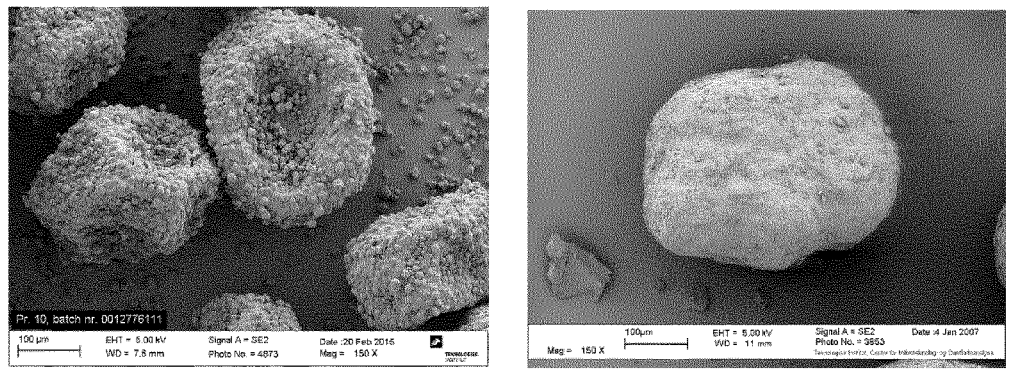
FIG. 1 shows a photographic picture of the surface morphology of a microcapsule of the invention (left picture) and of the commercially available lutein microcapsule FloraGLO® Lutein 10% VG TabGrade from Kemin Health, L.C (right picture), both photographic pictures being obtained by scanning electron microscopy.

In one embodiment of the microcapsule of the invention the content of said at least one active substance, calculated as free lutein, is from 1 to 20% of total weight of the microcapsule, preferably from 3 to 15% more preferably from 4 to 13%, for instance from 5 to 10% of total weight of the microcapsule.

In a second embodiment of the microcapsule of the invention it comprises at least one antioxidant e.g. selected from the group essentially consisting of or comprising t-butylhydroxytoluene (BHT), t-butylhydroxyanisole (BHA), ascorbic add, sodium ascorbate, citric acid, sodium citrate, EDTA or its salts, tocopherols, TBHQ, ethoxyquine, propyl gallate, and extracts from herbs, i.a. rosemary or oregano extract.

In a third embodiment of the microcapsule it comprises at least one plasticizer, e.g. selected from the group essentially consisting of or comprising carbohydrates and carbohydrate alcohols, examples of which are sucrose, glucose, fructose, lactose, invert sugar, glucose syrup, sorbitol, mannitol, trehalose, tagatose, pullulan, Raftilose (oligofructose), dextrin, maltodextrin, glycerin and mixtures thereof.

In a forth embodiment of the invention the microcapsule comprises fish gelatine of low bloom, medium bloom or high bloom. In a preferred version of the forth embodiment the microcapsule comprises low bloom fish gelatine having a strength of 30 bloom or less preferably of 20 bloom or less and more preferably of 10 bloom or less.

In a fifth embodiment the microcapsule comprises lutein ester(s) as active substance. In comparison with prior art products comprising microcapsules of free lutein this microcapsule has the further advantage that the lutein ester(s) is the naturally occurring form of the lutein. Producing free lutein from a marigold extract requires saponification under harsh conditions. This processing step is avoided when using lutein ester(s) in the microcapsule.

In a sixth embodiment the microcapsule is prepared form an emulsion of melted or dissolved lutein or lutein ester concentrate(s) in an aqueous solution of the fish gelatine in the absence of an emulsifier, wherein said lutein or lutein ester concentrate(s) is optionally melted or dissolved in an edible oil.

In a seventh embodiment of the microcapsule of the invention the lutein/lutein ester droplets have an average size D[4;3] determined by Fraunhofer diffraction of from 0.02 to 100 µm, preferably 0.05 to 50 µm, more preferred 0.1 to 5 µm or 0.2 to 1.5 µm; and in particular from 0.1 to 0.5 µm. The term D[4;3] is explained in the introduction to the examples.

In a $8^{th}$ embodiment the microcapsule is prepared from non-crystalline lutein ester.

The microcapsule may further contain conventional additives e.g. selected from the group essentially consisting of or comprising anti-caking agents, e.g. tri-calcium phosphate and silicates, i.a. silicon dioxide and sodium aluminium silicate.

The dividing and drying of the mixture of the oil-in-water preparation to produce a mass of particles can be done in any conventional way, such as spray cooling, modified spray cooling, spray drying, modified spray drying or sheet drying and crushing, see e.g. WO 91/06292 A1.

In one embodiment of the process of the invention the lutein or lutein ester concentrate(s) is melted or dissolved in edible oil, such as vegetable oil, e.g. selected from the group essentially consisting of or comprising sunflower oil, olive oil, cotton seed oil, safflower oil, MCT oil, palm oil or hydrogenated palm oil. Melting or dissolving the lutein or lutein ester in an oil facilitates dispersing and homogenising and reduces the temperature to be applied.

The process of the invention may in a second embodiment comprise a further step of homogenisation, such as high pressure homogenisation.

In a third embodiment of the process of the invention the aqueous solution of fish gelatine, preferably low bloom fish gelatine, is added to the melted or dissolved lutein or lutein ester concentrate(s) before homogenisation. Adding the aqueous phase to the oil phase minimizes physical loss of the lutein or lutein ester.

In a forth embodiment of the process the melted or dissolved lutein or lutein ester concentrate(s) is added to the aqueous solution of fish gelatine, preferably low bloom fish gelatine, before homogenisation.

In a fifth embodiment of the process the lutein or lutein ester concentrate(s) is added to the aqueous solution of fish gelatine, preferably low bloom fish gelatine, and melted during heating before homogenisation. This is preferred if the lutein or lutein ester is not melted or dissolved in oil before homogenisation because it is a more simple process and the physical loss is minimized.

In a sixth embodiment of the process of the invention the homogenisation continues until the lutein/lutein ester droplets have an average size D[4;3] determined by Fraunhofer diffraction of from 0.02 to 100 µm, preferably 0.05 to 50 µm, more preferred 0.1 to 5 µm or 0.2 to 1.5 µm; and in particular from 0.1 to 0.5 µm. The term D[4;3] is explained in the introduction to the examples.

In a seventh embodiment of the process lutein ester concentrate(s) is melted or dissolved. Lutein ester has a lower melting point than free lutein, and this makes it possible, in this embodiment of the invention, to melt or dissolve the lutein ester under atmospheric pressure and to use it directly in the process. This process includes less harsh conditions, and is therefore more cost effective than the process which uses free lutein.

Melting the lutein or lutein ester concentrate(s) is cost-effective since use of solvent can be economized. This in particular holds for lutein esters having a lower melting point compared to free lutein and thus need only small heating energy for melting.

The present invention also relates to a product comprising microcapsules of the invention or microcapsules produced according to the invention. Examples of such products are a tablet, a beverage, a dairy, a food, a food supplement, a pharmaceutical or veterinary product, a feed or feed supplement, a personal care product or a household product.

EXAMPLES

Determination of Content of Lutein Ester and Free Lutein

The content of lutein ester and free lutein in the microcapsules is determined as follows: The lutein or lutein ester is released from the microcapsules under mild alkaline conditions using alkalase and heat. The lutein or lutein ester is extracted by means of ethanol and diethyl ether in a ratio of 2:5 and an aliquot of this extraction is dissolved in a known volume of ethanol. The UV/Vis absorbance is measured at a specific wavelength and the concentration is calculated from a known extinction coefficient via Lambert-Beers equation.

When using the absorbance in lambda (max)=approx. 446 nm, the content of lutein ester in microcapsules containing lutein ester can be calculated by using the extinction coefficient $E^{1\%}_{1cm}=1373$. The corresponding content of free lutein can be calculated form the same measurement by using the extinction coefficient $E^{1\%}_{1cm}=2550$. For microcapsules containing free lutein the extinction coefficient $E^{1\%}_{1cm}=2550$ is used to calculate the content of free lutein.

Measuring of Particle Size (Oil Droplet Size)

Homogenisation is performed in conventional homogenisation equipment. Homogenisation takes place until the oil droplets have the intended average size D[4;3] determined by Fraunhofer diffraction. The term D[4;3] refers to the volume-weighted average diameter (see Operators Guide, Malvern Mastersizer 2000, Malvern Instruments Ltd., 1998/1999, UK, Chapter 6, page 6.3).

Evaluation of Particle Morphology

Scanning electron micrograph pictures at a magnification of 150× were prepared to evaluate the surface morphology of the microcapsules.

Measuring of Color Strength

An adequate amount of the formulation is dispersed in water in a water bath of 60-65° C. for 10 minutes followed by treatment in an ultrasonic bath for 5 minutes. The resulting dispersion is diluted to a final concentration of 5 ppm lutein ester and its UV/Vis absorption spectrum from 200-700 nm is measured in a quartz cuvette against water as a blank. From the resulting UV/Vis-spectrum the absorbance at the wavelength of maximum, $A_{max}$, is determined. The color strength ($E^{0.1\%}_{1cm}$) is calculated as follows: $E^{0.1\%}_{1cm}=$ ($A_{max}$)*dilution factor*0.1/(weight of sample in gram*lutein ester concentration in product in percent). The color strength ($E^{0.1\%}_{1cm}$) can also be calculated from the 5 ppm UV/Vis spectrum by multiplying the absorption in the wavelength of maximal absorption with 200.

Measuring of Tablet Stability

Multivitamin mineral tablets with a content of approximately 2 mg lutein ester (or 1 mg lutein) per tablet were prepared. The tablets were filled in HDPE containers sealed with an alumina lid. Some containers were stored at 40° C./75% RH for 6 months, some containers were stored at 25° C./60% RH for 12 months. The content of lutein/lutein ester in the tablets was analyzed after 3 and 6 months for the tablets stored at 40° C./75% RH and after 6 and 12 months for the tablets stored at 25° C./60% RH. The remaining lutein/lutein ester of the initial value was calculated in each timepoint.

Example 1

In vessel A 400 g dry low bloom, preferable zero bloom, fish gelatine, 400 g sucrose and 25 g sodium ascorbate were dissolved in 600 g water at 65° C. during stirring. In vessel B 250 g lutein ester concentrate was melted together with 62.5 g sunflower oil and 17.9 g mixed tocopherols (70% concentrate) at 60-90° C. The oily phase from vessel B was added to the aqueous phase in vessel A during stirring followed by homogenisation until the lutein ester droplets had an average particle size D[4;3] of less than 1.0 μm. The viscosity was adjusted with water and the dispersion was sprayed into native corn starch containing silicon dioxide as a flow agent. The formed particles were dried in air at 40-150° C. until the water content in the powder was below 5%.

The resulting dried powder had a content of 11.9% lutein esters corresponding to 6.4% free lutein determined by UV/Vis spectroscopy. The color strength ($E^{0.1\%}_{1cm}$) of the product was 91.

Example 2

In vessel A 400 g dry low bloom, preferable zero bloom, fish gelatine, 400 g sucrose and 25 g sodium ascorbate were dissolved in 600 g water at 65° C. during stirring. In vessel B 250 g lutein ester concentrate was melted together with 62.5 g sunflower oil and 17.9 g mixed tocopherols (70% concentrate) at 60-90° C. The oily phase from vessel B was added to the aqueous phase in vessel A during stirring followed by homogenisation until the lutein ester droplets had an average particle size D[4;3] of less than 1.0 μm. The viscosity was adjusted with water and the dispersion was sprayed into native corn starch containing silicon dioxide as a flow agent. The formed particles were dried in air at 40-150° C. until the water content in the powder was below 5%.

The resulting dried powder had a content of 12.4% lutein esters corresponding to 6.68% free lutein determined by UV/Vis spectroscopy. The color strength ($E^{0.1\%}_{1cm}$) of the product was 78.

Example 3

400 g dry low bloom, preferable zero bloom, fish gelatine, 400 g sucrose and 25 g sodium ascorbate were dissolved in 600 g water at 65° C. during stirring. 250 g lutein ester concentrate, 62.5 g sunflower oil and 17.9 g mixed tocopherols (70% concentrate) were added during stirring followed by homogenisation until the lutein ester droplets had an average particle size D[4;3] of less than 1.0 μm. The viscosity was adjusted with water and the dispersion was sprayed into native corn starch containing silicon dioxide as a flow agent. The formed particles were dried in air at 40-150° C. until the water content in the powder was below 5%.

The resulting dried powder had a content of 13.5% lutein esters corresponding to 7.27% free lutein determined by UV/Vis spectroscopy. The color strength ($E^{0.1\%}_{1cm}$) of the product was 86.

Example 4

In vessel A 1060 g dry low bloom, preferable zero bloom, fish gelatine, 1060 g sucrose and 62.5 g sodium ascorbate were dissolved in 1500 g water at 65° C. during stirring. In vessel B 625 g lutein ester concentrate was melted together with 62.5 g sunflower oil and 44.6 g d,l-α-tocopherol at 60-90° C. The aqueous phase from vessel A was added to the oil phase in vessel B during stirring followed by homogenisation until the lutein ester droplets had an average particle size D[4;3] of less than 1.0 μm. The viscosity was adjusted with water and the dispersion was sprayed into native corn starch containing silicon dioxide as a flow agent. The formed particles were dried in air at 40-150° C. until the water content in the powder was below 5%.

The resulting dried powder had a content of 11.1% lutein esters corresponding to 5.98% free lutein determined by UV/Vis spectroscopy. The color strength ($E^{0.1\%}_{1cm}$) of the product was 91.

Example 5

In vessel A 1251 g dry low bloom, preferable zero bloom, fish gelatine, 1251 g sucrose and 62.5 g sodium ascorbate were dissolved in 2063 g water at 65° C. during stirring. In vessel B 625 g lutein ester concentrate was melted together with 62.5 g sunflower oil and 44.6 g mixed tocopherols (70% concentrate) at 60-90° C. The aqueous phase from vessel A was added to the oil phase in vessel B during stirring followed by homogenisation until the lutein ester droplets had an average particle size D[4;3] of less than 1.0 μm. The viscosity was adjusted with water and the dispersion was sprayed into native corn starch containing tricalcium phosphate as a flow agent. The formed particles were dried in air at 40-15° C. until the water content in the powder was below 5%.

The resulting dried powder had a content of 10.8% lutein esters corresponding to 5.82% free lutein determined by UV/Vis spectroscopy. The color strength ($E^{0.1\%}_{1cm}$) of the product was 81.

The microcapsules prepared according to the examples were tested for stability in milk and beverages and the chemical stability of the lutein ester was tested in multivitamin mineral tablets as shown in the preamble to the examples and infra after the comparative example.

Comparative Example

The properties of products of the invention having a target of 10% lutein ester and prepared according to examples 1 and 4 were compared with a commercially available 10% lutein product from Kemin Health L.C. marketed as FloraGLO® Lutein 10% VG TabGrade™.

Figure 2:
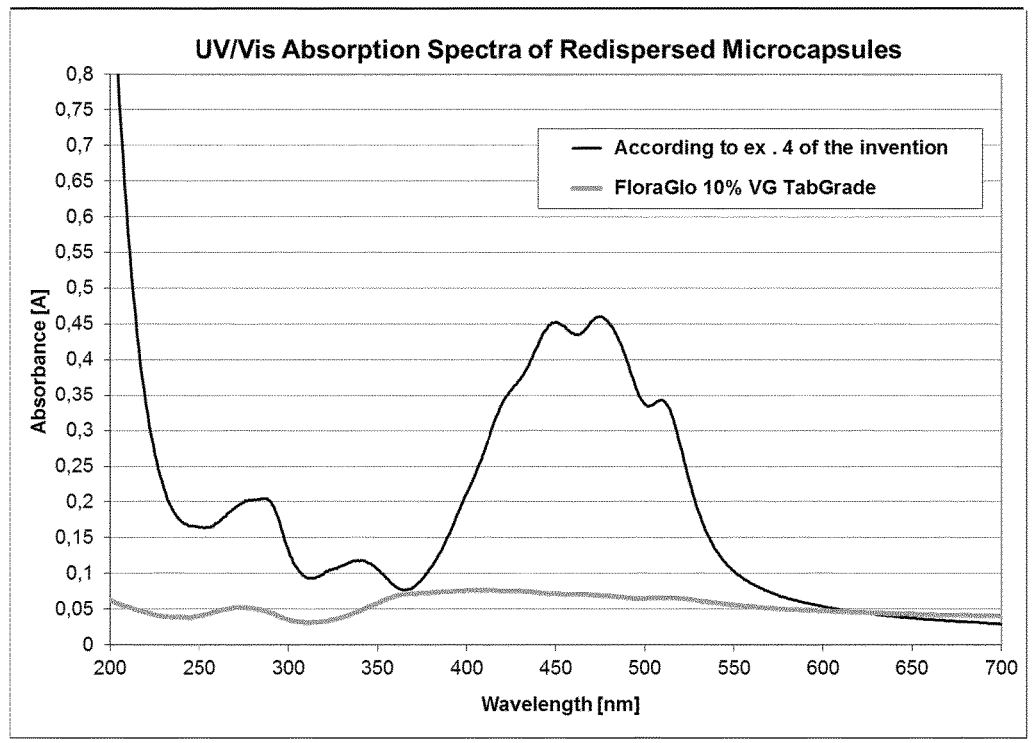
FIG. 2 shows UV/Vis absorption spectra of lutein ester microcapsules produced according to example 4 of the invention and of microcapsules FloraGLO® Lutein 10% VG TabGrade after respective re-dispersion in water. The concentration in the aqueous dispersion is 5 ppm lutein or lutein ester.

The comparative results for microcapsules and redispersed microcapsules are shown in FIGS. 1 and 2.

FIG. 1 shows scanning electron micrograph (SEM) pictures of the surface of microcapsules according to the invention (left) and of FloraGLO Lutein 10% VG TabGrade microcapsules (right). It can be clearly seen that the surface morphology of the microcapsules is different for the two types of microcapsules. A thin layer of insoluble starch covers the microcapsules of the invention and they have a rough structure compared to FloraGLO Lutein 10% VG TabGrade microcapsules, which are more smooth. Such rough structured microcapsules of the invention are more adapted for compression into tablets, since their compressibility is larger compared to smooth FloraGLO Lutein 10% VG TabGrade microcapsules.

FIG. 2 shows the UV/Vis-absorption spectra of redispersed microcapsules in a concentration of 5 ppm lutein or lutein ester. The upper black curve is the absorption spectrum of the redispersed microcapsules of example 4 of the invention, the lower grey curve is the absorption spectrum of redispersed FloraGLO 10% VG microcapsules from Kemin Health L.C. The color strength of the redispersed microcapsules can be calculated by multiplying the absorption at maximum wavelength with 200. It can be seen that the absorption is much higher for the microcapsules of the invention compared to FloraGLO® Lutein 10% VG TabGrade microcapsules. This means, that the color strength of redispersed microcapsules of the invention is much higher than that of the comparative redispersed product from Kemin Health L.C.

Example 6

Tablet Preparation

The chemical stability of the lutein ester microcapsules was tested by means of multivitamin mineral tablets having a content of about 2 mg of lutein ester per tablet. The tablets were packaged in high density polyethylene (HDPE) containers whose lids were sealed with heat-sealed aluminum foil. Some tablets were stored at 40° C. and 75% relative humidity for 6 months, some tablets were stored at 25° C. and 60% relative humidity for 12 months The lutein ester content was analyzed in each case after storage for 3 and 6 months at 40° C./75% RH and after 6 and 12 months at 26° C./60% RH The results were as shown in Table 1 below:

TABLE 1A

Tablet stability data, storage at 40° C./75% RH

| Ex | T = 0 % remaining | 3 months % remaining | 6 months % remaining |
|---|---|---|---|
| 1 | 100 | 95 | 93 |
| 4 | 100 | 104 | 95 |
| Comparative example (FloraGLO ® 10% VG TabGrade) | 100 | 81 | 78 |

TABLE 1B

Tablet stability data, storage at 25° C./60% RH

| Ex | T = 0 % remaining | 6 months % remaining | 12 months % remaining |
|---|---|---|---|
| 1 | 100 | 92 | 87 |
| 4 | 100 | 97 | 91 |
| Comparative example (FloraGLO ® 10% VG TabGrade) | 100 | 69 | 54 |

Figure 3A:
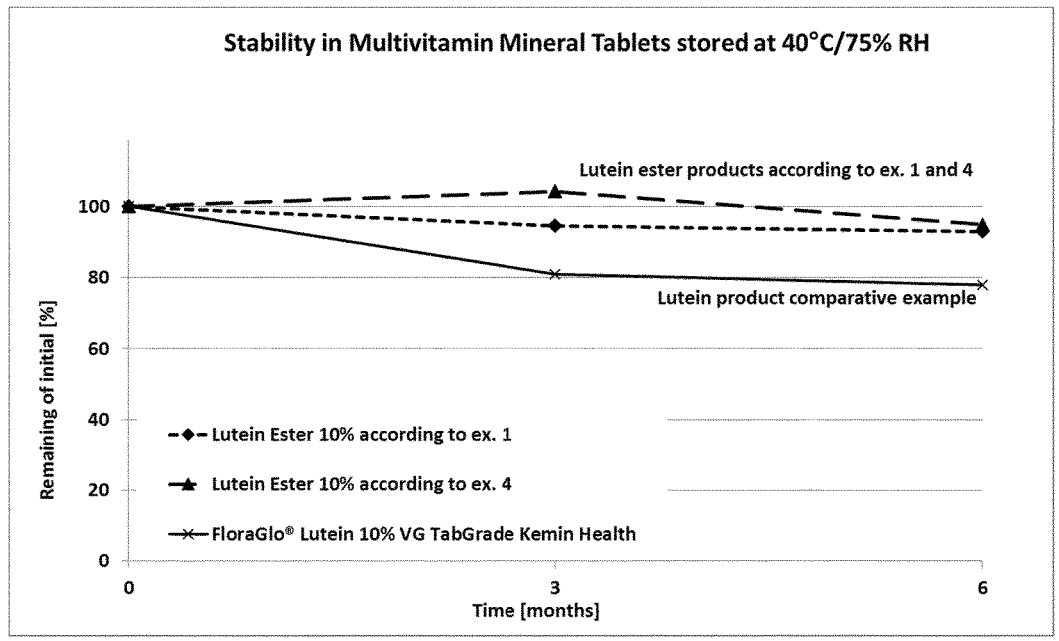
FIG. 3 shows tablet stability data of lutein ester products produced according to the invention and produced with FloraGLO® Lutein 10% VG TabGrade microcapsules from Kemin Health L.C. The multivitamin tablets were stored at 40° C./75% RH and at 25° C./60% RH, respectively, in sealed high density polyethylene containers (HDPE containers).
Figure 3B:
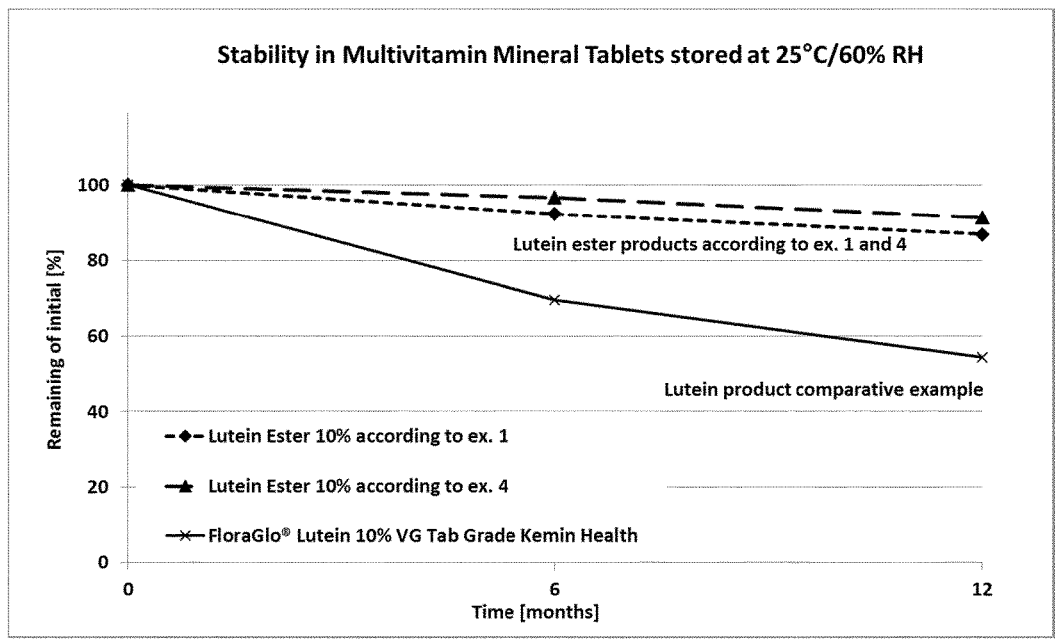

FIG. 3 graphically shows the chemical stability in multivitamin mineral tablets, as indicated in tables 1A and 1B, of microcapsules according to examples 2 and 4 of the invention and compared to multivitamin tablets of FloraGLO Lutein 10% VG TabGrade microcapsules. The tablets were stored in sealed HDPE-containers at 40° C./75% RH for 6 months (FIG. 3A) or at 25° C./60% RH for 12 months (FIG. 3B). It can be seen that the tablet stability of the microcapsules of the invention is much better than that of tablets formed of FloraGLO Lutein 10% VG TabGrade microcapsules. After 6 months at 40° C./75% RH the tablets containing microcapsules of the invention have lost approximately 5% of their activity whereas tablets containing FloraGLO 10% VG TabGrade microcapsules have lost approximate 20% of their activity. After 12 months at 25° C./60% RH the tablets containing microcapsules of the invention have lost approximately 10% of their activity whereas tablets containing FloraGLO Lutein 10% VG TabGrade have lost approximate 45% of their activity.

Example 7

Beverages Preparation

The stability of the lutein ester microcapsules in powder form was tested in two beverages, an orange juice and a sport beverage.

Orange Juice:

The orange juice was prepared from diluted orange juice concentrate with added ascorbic acid and sodium benzoate. Lutein ester microcapsules as a powder corresponding to a final concentration of 30 ppm lutein were dissolved in the concentrate. The solution was treated in a high pressure homogenizer at 100 bar and filled into bottles. The bottles were stored at room temperature and normal daylight for 1 month. The stability (ring formation) was evaluated visually every week.

Sport Beverage:

The sport beverage was prepared from carboxymethyl cellulose, water and a powder mix comprising calcium phosphate, potassium phosphate, sodium citrate, sodium chloride, sodium benzoate, potassium benzoate, citric acid, ascorbic acid and sucrose. Lutein ester powder corresponding to a final concentration of 5 ppm lutein were dissolved in water and added to the sport beverage followed by pasteurization in 60 seconds of the mixture. After cooling the bottles were filled and stored for 1 month at room temperature in normal daylight. The stability (ring formation) was evaluated visually every week.

The powders comprising microcapsules prepared according to examples 4 and 5 were tested in orange juice and sport beverage. After 1 month storage none of the samples showed ring formation in the beverages, i.e. the samples had sufficient stability in these applications.

Example 8

Milk Preparation

An amount of lutein ester microcapsules as powder corresponding to a concentration of 30 ppm lutein was dissolved in cold milk. The solution was heated to 60° C. and homogenized followed by pasteurisation at 95° C. in 10 minutes. The milk was filled into bottles and stored cold (below 10° C.) for 3 weeks. The stability (ring formation) was evaluated visually every week.

The powders comprising microcapsules prepared according to examples 1-4 were tested in milk. After 3 weeks storage none of the samples showed ring formation in milk i.e. the samples had sufficient stability in this application.

The invention is not reduced to the previously given examples but can be varied in many fold ways. For instance instead of lutein or lutein esters or in combination with said lutein or lutein esters the following carotenoids or its esters can also be used: zeaxanthin, beta-carotene, alpha-carotene, lycopene, astaxanthin, canthaxanthin, beta-cryptoxanthin, citranaxanthin and beta-apo-8'-carotenoids.

The invention claimed is:

1. A microcapsule comprising at least one active substance selected from lutein and lutein esters embedded in a matrix comprising a low fish bloom gelatin having a strength of 80 bloom or less as the sole agent with dispersing properties present, and optionally one or more other matrix components, wherein the content of said at least one active substance calculated as free lutein is from 0.5 to 25% of total weight of the microcapsule, and which microcapsule does not comprise any added emulsifier.

2. The microcapsule according to claim 1, wherein the content of said at least one active substance calculated as free lutein is from 1 to 20% of total weight of the microcapsule.

3. The microcapsule according to claims 1, wherein the content of said at least one active substance calculated as free lutein is from 3 to 15% of total weight of the microcapsule.

4. The microcapsule according to claim 1, wherein the content of said at least one active substance calculated as free lutein is from 4 to 13% of total weight of the microcapsule.

5. The microcapsule according to claim 1, wherein the content of said at least one active substance calculated as free lutein is from 5 to 10% of total weight of the microcapsule.

6. The microcapsule according to claim 1 further comprising at least one antioxidant and/or plasticizer.

7. The microcapsule according to claim 1, wherein said fish gelatin is a fish gelatine having a strength of 30 bloom or less.

8. The microcapsule according to claim 1, wherein said fish gelatin is a fish gelatine having a strength of zero bloom.

9. The microcapsule according to claim 1 prepared from an emulsion of melted or dissolved lutein or lutein ester concentrate in an aqueous solution of said fish gelatine in the absence of an emulsifier, wherein said lutein or lutein ester concentrate(s) is optionally melted or dissolved in an edible oil.

10. A process of preparing the microcapsule according to claim 1, which process comprises the steps of
melting or dissolving lutein or lutein ester concentrate(s),
providing an aqueous solution of said fish gelatine having a strength of 80 bloom or less as the sole agent with dispersing properties present, and said optionally other matrix components,
mixing said aqueous solution and said melted or dissolved lutein or lutein ester concentrate(s),
homogenizing the resulting preparation without addition of an emulsifier,
finely dividing and drying the mixture thus obtained to prepare a mass of particles each containing lutein or lutein ester(s) embedded in said fish gelatine.

11. The process according to claim 10, wherein the lutein ester concentrate(s) is melted or dissolved in edible oil, selected from the group consisting of sunflower oil, olive oil, cotton seed oil, safflower oil, MCT oil, palm oil and hydrogenated palm oil.

12. The process according to claim 10, wherein said aqueous solution of fish gelatin is added to said melted or dissolved lutein or lutein ester concentrate(s) before homogenization.

13. The process according to claim 10, wherein said melted or dissolved lutein or lutein ester concentrate(s) is added to said aqueous solution of fish gelatin before homogenization.

14. The process according to claim 10, comprising a further step of homogenization.

15. A microcapsule comprising at least one active substance selected from lutein and lutein esters embedded in a matrix comprising low boom fish gelatine having a strength of 80 bloom or less as the sole agent with dispersing properties present, and optionally one or more other matrix components, wherein the content of said at least one active substance calculated as free lutein is from 0.5 to 25% of total weight of the microcapsule, and which microcapsule does not comprise any added emulsifier obtainable by a process comprising the steps of
melting or dissolving lutein or lutein ester concentrate(s),
providing an aqueous solution of said low bloom fish gelatine and said optionally other matrix components,
mixing said aqueous solution and said melted or dissolved lutein or lutein ester concentrate(s),
homogenizing the resulting preparation without addition of an emulsifier,
finely dividing and drying the mixture thus obtained to prepare a mass of particles each containing lutein or lutein ester(s) embedded in said fish gelatine.

16. A product comprising the microcapsule according to claim 1.

17. The product according to claim 16, wherein the product is a tablet, a food, a food supplement, a beverage, a dairy, a pharmaceutical or veterinary product, a feed or feed supplement, a personal care products or a household product.

18. The product according to claim 16, wherein said product being selected from the group consisting of tablet, dairy and beverage and said fish gelatine is present and has a strength of 30 bloom or less.

19. The microcapsule according to claim 1, wherein said fish gelatin is a fish gelatine having a strength of 50 bloom or less.

20. A microcapsule consisting essentially of at least one active substance selected from lutein and lutein esters embedded in a matrix consisting essentially of a low fish bloom gelatin having a strength of 80 bloom or less and optionally one or more other matrix components, wherein the content of said at least one active substance calculated as free lutein is from 0.5 to 25% of total weight of the microcapsule, and which microcapsule does not comprise any added emulsifier.

\* \* \* \* \*